United States Patent [19]

Perrone et al.

[11] Patent Number: 4,837,215
[45] Date of Patent: Jun. 6, 1989

[54] PENEM DERIVATIVES

[75] Inventors: Ettore Perrone; Marco Alpegiani; Angelo Bedeschi, all of Milan; Franco Zarini, Settimo Milanese; Giovanni Franceschi, Milan; Costantino D. Bruna, Rho, all of Italy

[73] Assignee: Farmitalia Carlo Erba, Milan, Italy

[21] Appl. No.: 849,388

[22] Filed: Apr. 8, 1986

[30] Foreign Application Priority Data

Apr. 10, 1985 [GB] United Kingdom ............... 8509181

[51] Int. Cl.$^4$ .................. C07D 499/00; A61R 31/425
[52] U.S. Cl. .................................. 514/192; 514/195; 540/310
[58] Field of Search .................. 540/310; 514/192, 195

[56] References Cited

U.S. PATENT DOCUMENTS 4,623,643  11/1986  Alpegiani et al. ............... 540/310

FOREIGN PATENT DOCUMENTS 0118875  9/1984  European Pat. Off. .
0123650  10/1984  European Pat. Off. .
0132101  1/1985  European Pat. Off. .

OTHER PUBLICATIONS

Chemical Abstracts, vol. 99, No. 3, Jul. 18, 1983, pp. 595, Abstract 22228b Columbus, Ohio (U.S.).

Primary Examiner—Nicholas S. Rizzo
Attorney, Agent, or Firm—Oblon, Spivak, McClelland, Maier, & Neustadt

[57] ABSTRACT

Compounds of the following formula I

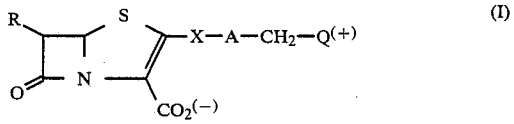

wherein
X represents a sulphur or an oxygen atom,
R is hydrogen or a $C_1$–$C_4$ alkyl group either unsubstituted or substituted by one or more substituents chosen from a free or protected hydroxy group and halogen atom;

A is a Z, Z—O—CO— or —Z—CO— residue, wherein Z represents
(a) an optionally substituted phenylene or naphthylene group,
(b) an optionally substituted heterocyclediyl radical wherein the hetero ring is mono or bicyclic, saturated or unsaturated containing at least one heteroatom selected from the group of oxygen, sulphur and nitrogen;
(c) an optionally substituted linear or branched $C_1$–$C_7$ alkylene radical;
(d) a $C_2$–$C_4$ alkenylene or alkynylene group or a group of formula

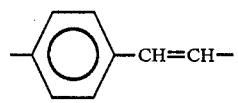

(e) an optionally substituted $C_3$–$C_8$ cycloalkylene ring;
(f) an aralkylene radical of the formula

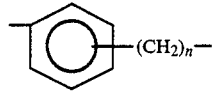

wherein
n is 1, 2 or 3; and
$Q^{(+)}$ represents a $+NR_1R_2R_3$ group, wherein
(i) $R_1$, $R_2$, $R_3$, are each independently an optionally substituted alkyl, aralkyl or aryl radical; or p1 (ii) $R_1$ is as defined above under (i) and $R_2$, $R_3$ taken together with the nitrogen atom represent an optionally substituted heterocyclic or fused heterocyclic radical; or
(iii) $R_1$, $R_2$, $R_3$, taken together with the nitrogen atom, represent an optionally substituted azoniabicyclo or azoniatricyclo radical; or
(iv) $R_1$, $R_2$, $R_3$, taken together with nitrogen atom, represent an optionally substituted pyridinium, pirazinium, pyrazolium, or pyridazinium radical, such radicals being optionally fused with one phenyl ring or with a 5–7 membered, saturated or unsaturated cycloaliphatic or heterocyclic ring, or a pharmaceutically or veterinarily acceptable salt thereof having high antibacterial activity.

35 Claims, No Drawings

PENEM DERIVATIVES

BACKGROUND OF THE INVENTION

1. Field of the Invention

The present invention relates to new penem compounds, to processes for their preparation, and to pharmaceutical and veterinary compositions containing them.

2. Discussion of the Background

Antibiotics are important chemotherapeutic agents, and their development over the past 25 years has produced a major new industry. Antibiotics have revolutionized the practice of medicine by bringing under control bacterial infectious diseases. Despite the continual development of new antibiotics, most antibiotics are effective against a rather narrow range of bacteria. Moreover the wide spread use of antibiotics has given rise to new resistant strains of bacteria. Accordingly, there is a continuing need for the development of new potent, broad spectrum antibacterial agents.

A particularly important group of antibacterial agents are the penem compounds. Numerous penem derivatives are known, however, like antibacterial agents in general, these penem compounds are generally effective against a rather narrow group of bacteria. Additionally, bacteria may become resistant to particular penem compounds if the compound is used continuously over a long period of time. Therefore, there is a continual need for the development of new penem compounds which are potent antibiotics and exhibit a broad spectrum of activity.

SUMMARY OF THE INVENTION

Accordingly, it is an object of this invention to provide a novel class of penem compounds, or salts thereof.

It is another object of this invention to provide a pharmaceutical composition containing at least one of these novel penem compounds.

It is another object of the invention to provide a veterinary composition containing at least one of these novel penem compounds.

It is another object of this invention to provide a novel class of potent broad spectrum antibacterial agents.

It is another object of this invention to provide a novel class of penem compounds having markedly increased in vitro activity against Gram-positive bacterial strains.

It is another object of this invention to provide a novel class of penem compounds having markedly increased in vitro activity against Gram-negative bacterial strains.

It is another object of this invention to provide a novel class of penem compounds having markedly increased in vitro activity against Gram-positive and Gram-negative bacterial strains.

It is another object of this invention to provide a novel class of penem compounds which shows unusually long plasma levels.

It is another object of this invention to provide a novel class of penem compounds which have negligible toxicity.

It is another object of this invention to provide a novel class of penem compounds which are useful as nutritional supplements in animal feeds.

It is still another object of this invention to provide a novel class of penem compounds which are useful in a prophylactic manner, as cleaning or surface disinfecting compositions.

The present inventors have now surprisingly discovered a novel class of penem compounds which satisfy all of the above objects of this invention and other objects which will become apparent from the description of the invention given hereinbelow.

Accordingly, the present invention relates to compounds which are quaternary ammonium carboxylates of the following formula (I) and their pharmaceutically or veterinarily acceptable salts,

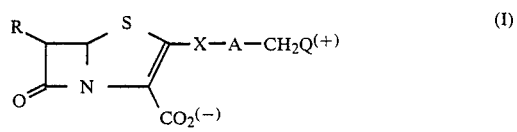

X represents an oxygen or sulphur atom.

R is a hydrogen atom or a $C_1$-$C_4$ alkyl group which is either unsubstituted or substituted by one or more substituents chosen from the group consisting of a free hydroxy group, protected hydroxy groups and halogen atoms.

A is a Z, Z—O—CO— or —Z—CO— residue, where

Z represents (a) an unsubstituted or a substituted phenylene or naphthylene group, (b) an unsubstituted or substituted heterocyclediyl radical where the hereto ring is mono or bicyclic, saturated or unsaturated and contains at least one heteroatom selected from the group consisting of oxygen, sulphur and nitrogen;

(c) an unsubstituted or substituted linear or branched $C_1$-$C_7$ alkylene radical;

(d) a $C_2$-$C_4$ alkenylene or alkynylene group or a group of the formula

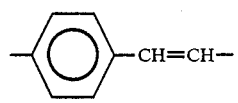

(e) an unsubstituted or substituted $C_3$-$C_8$ cycloalkylene ring;

(f) an aralkylene radical of formula

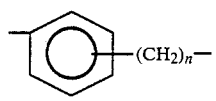

wherein n is 1, 2 or 3, and $Q(+)$ represents a $+NR_1R_2R_3$ group, wherein (i) $R_1$, $R_2$ and $R_3$ are each independently an unsubstituted or substituted alkyl, aralkyl or aryl radical; or (ii) $R_1$ is as defined above under (i) and $R_2$ and $R_3$ taken together with the nitrogen atom to which they are both bound represent an unsubstituted or substituted heterocyclic or fused heterocyclic radical; or (iii) $R_1$, $R_2$ and $R_3$, taken together with the nitrogen atom to which they are all bound, represent an unsubstituted or substituted azoniabicyclo or azoniatricyclo radical; or (iv) $R_1$, $R_2$ and $R_3$, taken together with the nitrogen atom to which they are all bound, represent an unsubstituted or substituted pyridinium, pirazinium, pyrazolium, or pyridazinium radical, such radicals being optionally fused with one phenyl ring or with a 5-7 membered, saturated or unsaturated cycloaliphatic or heterocylic ring.

The present invention further relates to pharmaceutical or veterinary compositions containing at least one of the novel class of penems of this invention in association with a pharmaceutically or a veterinarily acceptable excipient. The present invention also relates to the administration of these compounds to a patient in need thereof.

DESCRIPTION OF THE PREFERRED EMBODIMENTS

The present invention includes all the possible geometrical and optical isomers of the compounds of formula (I), either in the form of someric mixtures or in the form of the individual separated isomers. Preferably, the compounds of formula (I) having a (5R, S) configuration. The preferred R group is an (α-hydroxy)ethyl radical and this radical preferably has a (1R) configuration, i.e. a R configuration at the α-carbon atom of the ethyl group.

The pharmaceutically or veterinarily acceptable salts of the compounds of formula (I) are also included within the scope of the invention. The salts may be salts with acids, either inorganic acids such as, e.g., hydrochloric, hydrobromic, sulphuric or phosphoric acid, or organic acids such as acetic, citric, tartaric, fumaric or methanesulphonic acid, and salts with bases, either inorganic bases such as alkali or alkaline-earth metal hydroxides, in particular sodium and potassium hydroxides, or organic bases such as triethylamine, pyridine, benzylamine or collidine, including aminoacids such as lysine or procaine. The invention also includes inner salts, i.e. zwitterions. In the present specification, the term "halogen" preferably encompasses fluorine and chlorine atom, but also includes iodine and bromine atoms.

The alkyl groups, including the aliphatic moieties of the alkoxy, alkylthio and alkanoyl groups, may be branched or straight chain. Preferably, the alkyl and aralkyl radicals under definition (i) for Q above are unsubstituted or substituted $C_1$-$C_4$ alkyl and $C_7$-$C_{11}$ aralkyl radicals. In the definitions of Z, $R_1$, $R_2$, $R_3$, the substituents for the mentioned alkyl, aralkyl, aryl, azoniabicyclo, azoniatricyclo, pyridinium, pyrazinium, pyrazolium, pyridazinium, cycloalkylene, alkylene, phenylene, naphthylene and heterocylediyl radicals are preferably selected from the group consisting of: (a) halogen; (b) hydroxy; (c) $C_1$-$C_4$ alkoxy; (d) $C_1$-$C_4$ alkylthio; (e) a group —$NR_4R_5$ where each of $R_4$ and $R_5$ is, independently, hydrogen or $C_1$-$C_4$ alkyl; (f) sulfo; (g) —$CO_2R_4$ where R is as defined above; (h) —C≡N; (i) dimethyl-formimdino; (j) a group —CO—$NR_4R_5$ where $R_4$ and $R_5$ are as defined above; (k) carbamoyloxy; (l) a hydroxyiminomethyl (HO—N=CH—) or methoxyiminomethyl ($CH_3O$—N=CH—) group; (m) a formamido or acetoamido group; (n) a formyloxy or acetoxy group; (o) a $C_1$-$C_4$ alkanoyl group; (p) an aryl group; (q) a saturated or unsaturated heterocyclic ring; (r) a nitro group; (s) a mesyloxy group; (t) an oxo group; and (u) a $C_1$-$C_4$ alkyl group either unsubstituted or substituted by a substituent chosen from (a) to (t) above.

The $C_1$-$C_4$ alkyl group is, preferably, methyl or ethyl. The heterocylediyl radical is, preferably, furanediyl, 1,3 thiadiazolediyl, thiophenediyl or pyridinediyl The $C_1$-$C_7$ alkylene radical is preferably methylene, ethylene, propylene or butylene group. The $C_3$-$C_8$ cycloalkylene ring is, preferably, cyclobutylene cyclopentylene or cyclohexylene. The $C_2$-$C_4$ alkylene group is, preferably, a 1,2-ethenylene group and the $C_2$-$C_4$ alkynylene group is, preferably, an ethynylene group.

The term "aryl" encompasses, preferably, phenyl and naphthyl groups. The heterocyclic rings may be saturated or unsaturated, may have from 4 to 7 members and may contain from 1 to 4 heteroatoms selected from oxygen, nitrogen and sulphur atoms.

The $C_1$-$C_4$ alkoxy group is, preferably, methoxy or ethoxy. The $C_1$-$C_4$ alkylthio group is, preferably, methylthio or ethylthio and the $C_1$-$C_2$ alkanoyl group is, preferably, acetyl or propionyl.

The protected hydroxy group may be a hydroxy group protected by a protecting group chosen, for instance, from an unsubstituted or substituted especially halosubstituted, acyl group, e.g., acetyl, monochloroacetyl, dichloroacetyl, trifluoroacetyl, benzoyl or p-bromophenacyl; a triarylmethyl group, in particular triphenylmethyl; a silyl group, in particular trimethylsilyl, dimethyl-tert-butylsilyl, diphenyl-tert-butyl silyl; or also a group such as tert-butoxy carbonyl, p-nitrobenzyloxycarbonyl, 2,2,2-trichloroethoxycarbonyl, allyloxycarbonyl, benzyloxycarbonyl, and pyranyl.

Preferred protecting groups of the hydroxy function are p-nitro-benzyloxycarbonyl; dimethyl-tert-butylsilyl; diphenyl-tert-butyl-silyl; trimethyl silyl; allyloxycarbonyl; benzyloxycarbonyl; p-bromophenacyl; triphenylmethyl and pyranyl groups.

Preferred classes of compounds under this invention include compounds of formula (I) where:

R is an (hydroxy)ethyl group; X is as defined above; and

Z is one of the following residues:

(a')

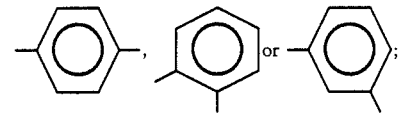

(b')

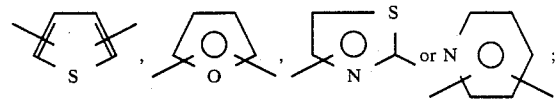

(c') methylene, ethylene, n-propylene or tetramethylene group;

(d') 1,2 ethenediyl group;

(e')

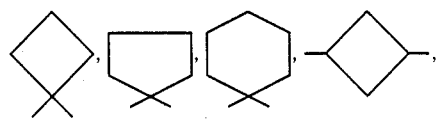

-continued

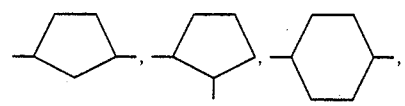

(f')

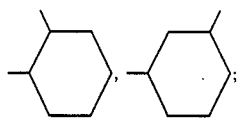

Q(+) is +NR₁R₂R₃, where (i') R₁, R₂ and R₃ are each independently methyl, ethyl, n-propyl, i-propyl, dimethylaminomethyl, cyanomethyl, cyanoethyl, carbamoylmethyl, 2-hydroxyethyl, 2-chloroethyl, carboxymethyl, ethoxycarbonylmethyl, carboxyethyl, 2-methyl-2-cyanoethyl, 3-oxobutyl or dimethylformimidino group —C(-NMe₂)=NH; or (ii') R₁ is as defined above under (i') and still preferably methyl, ethyl, chloroethyl, cyanomethyl, cyanoethyl, hydroxyethyl or aminoethyl, and R₂ and R₃, taken together with the nitrogen atom to which both are bound, represent one of the following heterocyclyl ammonium radicals

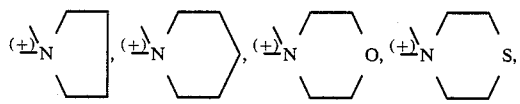

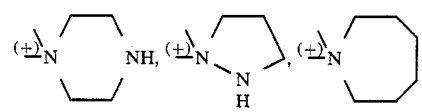

and in the heterocyclic ring, when substituted, the substituents are one or more, preferably one or two, are equal or different and are selected from the group (a), (b), (e), (g), (h), (i), (q), (t) ,and (u) as defined above; or (iii') R₁, R₂ and R₃, taken together with the nitrogen atom to which all are bound, represent one of the following radicals

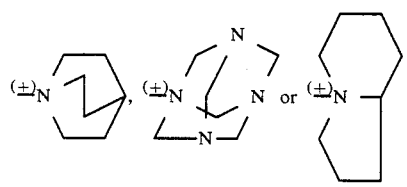

where the quinuclidine ring may be substituted by an oxo, hydroxy or methoxy group; or (iv') R₁, R₂ and R₃, taken together with the nitrogen atom to which they are all bound, represent one of the following radicals

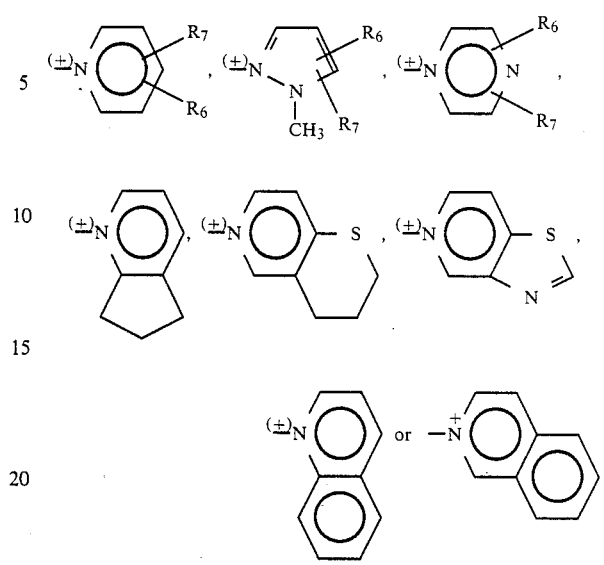

where R₆ and R₇ are each independently a hydrogen atom, C₁–C₄ alkyl, cyanomethyl, methylsulphonyl, carbamoyl, hydroxymethyl, methylthio, or methoxy group.

Preferred compounds also include pharmaceutically or veterinarily acceptable salts of the compounds described above.

Specific examples of preferred embodiments of the invention are listed in the following table:

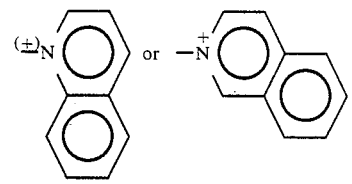

| Compound | X | —A— | Q(+) |
|---|---|---|---|
| 1 | S | —CH₂— | 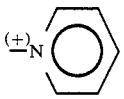 pyridinium |
| 2 | S | —CH₂— | 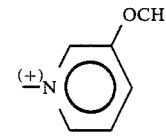 OCH₃-pyridinium |
| 3 | S | —CH₂— | 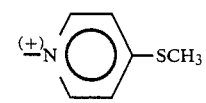 pyridinium-SCH₃ |
| 4 | S | —CH₂— | 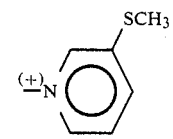 SCH₃-pyridinium |

-continued
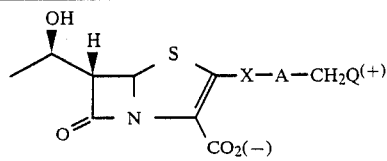
| Compound | X | —A— | Q(+) |
|---|---|---|---|
| 5 | S | —CH₂— | 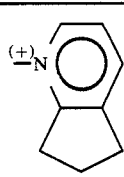 |
| 6 | S | —CH₂— | 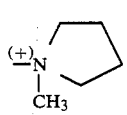 |
| 7 | S | —CH₂— | 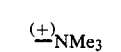 |
| 8 | S | —CH₂— | 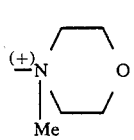 |
| 9 | S | —CH₂CH₂— | 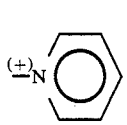 |
| 10 | S | —CH₂CH₂— | 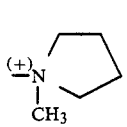 |
| 11 | S |  | 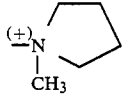 |
| 12 | S | 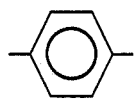 | 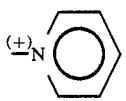 |
| 13 | S |  | 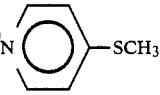 |
| 14 | S |  | 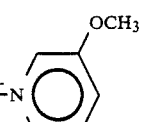 |
| 15 | S |  | 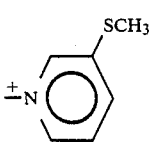 |
-continued
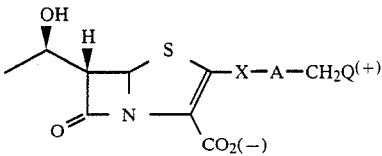
| Compound | X | —A— | Q(+) |
|---|---|---|---|
| 16 | S | 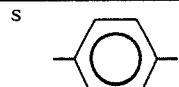 | 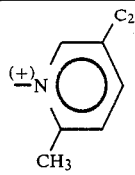 |
| 17 | S | 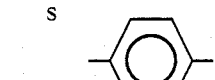 | 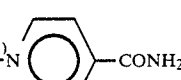 |
| 18 | S | 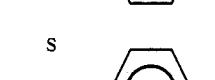 | 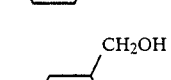 |
| 19 | S |  |  |
| 20 | S | 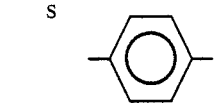 | 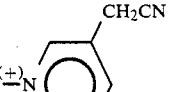 |
| 21 | S |  |  |
| 22 | S | 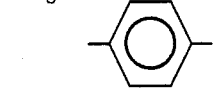 | 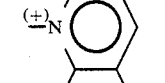 |
| 23 | S |  | 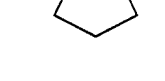 |
| 24 | S | 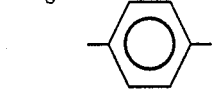 | 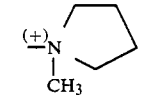 |
| 25 | S | 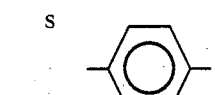 | 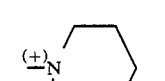 |

-continued

![Structure showing penem with X—A—CH2Q(+)]

| Compound | X | —A— | Q(+) |
|---|---|---|---|
| 26 | S | 2,3-dimethylphenyl | pyridinium |
| 27 | S | 2,3-dimethylphenyl | N-methylpyrrolidinium |
| 28 | S | 3,4-dimethylphenyl | pyridinium |
| 29 | S | 3,4-dimethylphenyl | N-methylpiperidinium |
| 30 | S | 3-methylphenyl | NMe3(+) |
| 31 | O | 1,4-phenylene | pyridinium |
| 32 | O | 1,4-phenylene | 3-(cyanomethyl)pyridinium |
| 33 | O | 1,4-phenylene | 3-(methylthio)pyridinium |
| 34 | O | 1,4-phenylene | 3-methoxypyridinium |
| 35 | O | 1,4-phenylene | NEt3(+) |
| 36 | O | 1,4-phenylene | N-methylpyrrolidinium |
| 37 | O | 1,4-phenylene | N-methylmorpholinium |
| 38 | O | 3-methylphenyl | pyridinium |
| 39 | O | 3,4-dimethylphenyl | pyridinium |
| 40 | O | 1,4-phenylene | 4-methoxypyridinium |
| 41 | O | 1,4-phenylene | 2-methoxypyridinium |

The compounds of formula (I) can be prepared by a process comprising the steps of reacting a compound of formula (II)

(II)

where $R_1$, $R_2$ and $R_3$ are as defined above, with a penem intermediate of formula (III)

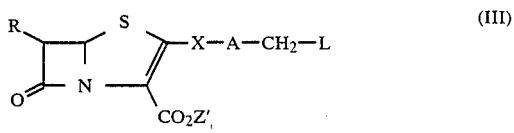

(III)

where R, X and A are as defined above, Z' is a carboxy protecting group, and L is a leaving group susceptible to nucleophilic displacement by the amine of formula (II). Then, removing the protecting groups and, if desired, separating a mixture of isomers into the single isomers.

The leaving group L in the compound of formula (II) may be, for example, a sulphonyloxy group —OSO₂R', where R' is a substituted or unsubstituted alkyl or aryl group; or a halogen atom such as iodine, bromine, or chlorine. A particularly preferred sulphonyloxy group is trifluoromethanesulphonyloxy, —OSO₂CF₃. A particularly preferred halogen atom is iodine. The carboxy protecting group Z' may be any group which, together with the —CO₂— moiety, forms an esterified carboxy group. Examples of carboxy protecting groups are, in particular, $C_1$–$C_6$ alkyl groups, for instance methyl, ethyl or tert-butyl; halo-substituted $C_1$–$C_6$ alkyl groups, for example 2,2,2-trichloroethyl; $C_2$–$C_4$ alkenyl groups, for example allyl; unsubstituted or substituted aryl groups, for example phenyl and p-nitro-phenyl; unsubstituted or substituted aryl $C_1$–$C_6$ alkyl groups, for example benzyl, p-nitro-benzyl and p-methoxy-benzyl; aryloxy-$C_1$–$C_6$ alkyl groups, for example phenoxyethyl; or groups such as benzhydryl, o-nitrobenzyhydryl, acetonyl, trimethylsilyl, diphenyl-tert-butyl-silyl, dimethyl-tert-butyl-silyl, pivaloyloxy methyl or phthalidyl. Particularly preferred carboxy protecting groups are allyl, p-nitrobenzyl, trimethylsilyl, dimethyl-tert-butyl-silyl, and trichloroethyl.

When in a compound of formula (III), R is a $C_1$–$C_3$ alkyl group substituted by hydroxy, the hydroxy is preferably protected. A particularly preferred protecting group is dimethyl-tert-butyl-silyl.

The reaction between a compound of formula (II) and a compound of formula (III) may be performed in a suitable organic, preferably aprotic, solvent which may be, for instance, tetrahydrofuran, dimethylformamide, acetone or a halogenated hydrocarbon such as, dichloromethane. The reaction temperature may vary between about −100° C. and about +40° C., preferably between −70° C. and +15° C. A compound of formula (III) where L is a sulphonyloxy group may be prepared by reacting, according to known and conventional procedures, a carbinol precursor of formula (IV)

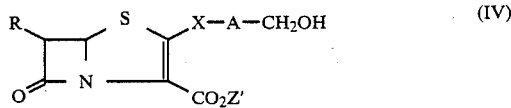

where R, X, A and Z' are as defined above, with the appropriate sulphonyl anhydride or sulphonyl halide, preferably triflic anhydride, or triflic chloride. The reaction is performed in the presence of a non-nucleophilic acid acceptor which may be, for instance, an inorganic base such as calcium or lithium carbonate, or calcium oxide, or an organic base such as 2,6-lutidine or the same compound of formula (II) to be reacted in the subsequent step.

Indeed, according to a preferred procedure of the invention, the compound of formula (IV) is made to react with the suitable sulphonyl anhydride or sulphonyl halide in the presence of an excess, usually an amount equal to or greater than 2 molar equivalents, of the desired compound of formula (II). In this situation, the compound of formula (III) is not even isolated from the reaction mixture because it reacts in situ with the compound of formula (II).

The preferred procedure mentioned above is preferably carried out using dry dichloromethane as solvent at temperatures from about −70° C. to +25° C.

When a compound of formula (II) is reacted with a compound of formula (III) where L is halogen, the presence of a silver salt, particularly if soluble in the media, e.g. AgClO₄, may be beneficial.

A compound of formula (III) where L is halogen, may be prepared from the corresponding carbinol precursor of formula (IV) according to a modified Mitsunobu reaction. In the Mitsunobu reaction, the carbinol is allowed to react with an organic amine hydrohalide, such as methoxyamine hydrochloride, pyridine hydrochloride, pyridine hydrobromide and the preformed complex obtained from diethylazodicarboxylate and triphenylphosphine. The reaction is carried out in tetrahydrofuran or methylene chloride, for example, preferably around room temperature.

Alternatively, in the above modified Mitsunobu reaction, a zinc halide, such as zinc chloride, zinc bromide or zinc iodide, can be substituted for the organic amine hydrohalide under conditions substantially similar to those reported in *J. Org. Chem.*, 1984, 49, 3027.

Alternatively, a compound of formula (III) where L is halogen may be obtained from the carbinol of formula (IV) according to the more conventional procedures. These procedures entail a reaction with inorganic acid halides, for example, SOCl₂, PCl₅, PCl₃, PBr₃, POCl₃ and POBr₃.

An additional methodology well-known in the literature, namely the reaction with PPh₃ in CCl₄, can be exploited for the preparation of compounds of formula (III) where L is chloride. A compound of formula (III) where L is iodine can be prepared by a halide exchange reaction from a compound of formula (III) where L is chlorine or bromine and sodium iodide. This reaction is preferably carried out in acetone at temperatures ranging from 0° C. to +60° C. (reflux temperature). Some intermediates of formula (III), preferably when L is chlorine, and the intermediates of formula (IV), either as such or as their protected derivatives, are known compounds or can be prepared from known compounds by following known general methodologies. These include, for example, the following:

(A) Thermal cyclization of a compound of formula (V)

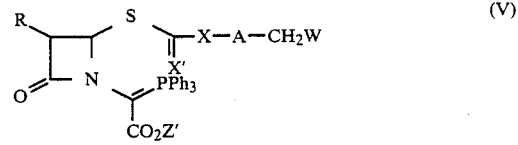

where R, X, A and Z' are as defined above, X' is a sulphur or oxygen atom, and W is a free or protected OH, or a halogen atom, preferably chlorine, according to the method described, for example, in *J. Am. Chem. Soc.*, 1978, 100, 8214 and *Chem. Pharm. Bull.*, 1981, 29, 3158.

(B) Thermal cyclization of a compound of formula (VI)

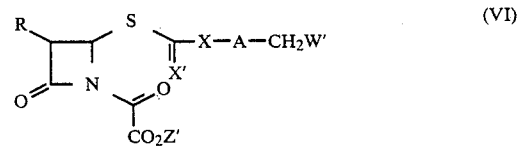

where R, X, X', A and Z' are as defined above, and W' is free or protected OH. The cyclization is performed in the presence of an organic phosphite, preferably trimethyl or triethyl phosphite, according to the method described, for example in *Chem. Pharm. Bull.*, 1983, 31, 768 and *Tetrahedron Lett.*, 1984, 25, 2395.

(C) Condensation of a 2-thioxopenam of formula VII, either as such or in its thioenol form or as a salt thereof and

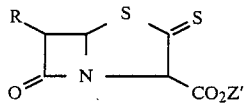

where R and Z' are as described above, with a reagent of formula (VIII)

where L, A and W' are as defined above, according to the method described, for example in *J. Chem. Soc., Chem. Comm.*, 1982, 713.

(D) reaction of a 2-sulphinyl penem of formula (IX)

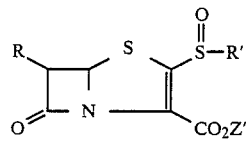

where R and X' are as defined above, and R' is an unsubstituted or substituted alkyl, aryl or aralkyl group, with a reagent of the formula (X)

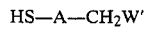

where A and W' are as defined above, according to the method described, for example, in *Tetrahedron Lett.*, 1982, 23, 3535.

(E) Cyclization of a compound of formula (XI)

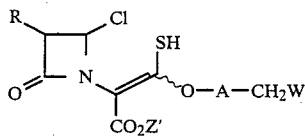

where R, A, W and Z' are a defined above. The cyclization occurs spontaneously, preferably in the presence of a mild base, following unmasking of the —SH moiety from a protected derivative thereof, according to the method described, for example, in *J. Chem. Soc., Chem. Commun.*, 1983, 1005.

(F) Reaction of a compound of formula (XII)

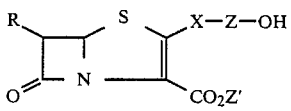

where R, X, Z and Z' are as defined above with a carboxylic acid of formula (XIII), or an activated derivative thereof,

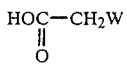

were W is as defined above, according to the method described, for example, in our British Patent Application No. 2,118,181 A which is hereby incorporated by reference.

In particular, method (A) may be used to obtain intermediates for formula (III) and (IV) were X represents a sulphur atom. Methods (B), (C) and (D) may be used to obtain intermediates of formula (IV) where X represents a sulphur atom. Method (E) may be used to obtain intermediates of formula (III) and (IV) where X represents an oxygen atom and method (F) may be used to obtain intermediates of formula (III) and (IV) where —A— represents a group

Removal of protecting groups can be effected by known per se procedures. For example, silyl groups can be removed under mild acidic conditions, or by fluoride ions, e.g. with tetrabutylammonium fluoride. p-Nitrobenzyl groups can be removed by reduction, e.g. by catalytic hydrogenation, or with metals, such as Fe and Zn. Allyl carboxylates can be cleaved by transallylation with an organic acid or a salt thereof, such as acetic acid, 2-ethylhexanoic acid or their sodium and potassium salts. This reaction is catalyzed by a triphenylphosphine-palladium complex, preferably by tetrakis-triphenylphosphine-Pd°.

The optional salification of an obtained compound and the separation of a mixture of isomers into single isomers may be carried out following known and conventional procedures.

Compounds of formula (II), (V), (VI), (VII), (VIII), (IX), (X), (XI), (XII) and (XIII) are known compounds or can be prepared from known compounds according to known methods. The compounds of formula (I) provided by the present invention are potent, broad spectrum antibacterial agents.

In comparison with other penem compounds, e.g. the sodium salts derived from penems of formula (IV), or compounds of formula (I) where Q is an amine instead of quaternary ammonium, they usually show markedly increased in vitro activity against both Gram-positive and Gram-negative strains.

Moreover, in comparison with other penem compounds, they show unusually prolonged plasma levels. When tested in vivo after parenteral administration, they display a very high degree of therapeutic effectiveness in treating infections caused by both Gram-positive and Gram-negative bacteria. Their toxicity on the other hand is quite negligible.

The following table shows the activity of two typical compounds of formula (I), the Compounds (1) and (31) of the previous table.

| Organism | Comparison between the antibacterial in vitro activity (MIC, μg/ml) of compounds (1) and (31) and a reference drug: Moxalactam | | |
|---|---|---|---|
|  | Compound (1) | Compound (31) | MOXA-LACTAM |
| *Staphylococcus aureus* | 0.222 | 0.045 | 0.31 |

-continued

Comparison between the antibacterial in vitro activity (MIC, μg/ml) of compounds (1) and (31) and a reference drug: Moxalactam

| Organism | Compound (1) | Compound (31) | MOXA-LACTAM |
|---|---|---|---|
| Smith ATCC 13709 *Staphylococcus aureus* 209 P | 0.011 | 0.022 | 0.31 |
| *Streptococcus pyrogenes* ATCC 12384 | ≦0.005 | 0.011 | 2.5 |
| *Klebsiella aerogenes* 1082E (β-lact.+) | 0.78 | 1.56 | 0.78 |
| *Enterobacter cloacae* P 99 (β-lact.+) | 0.78 | 1.56 | 3.12 |
| *Escherichia coli* B Cef. R (β-lact.+) | 0.78 | 1.56 | 2.5 |
| *Escherichia coli* 026/B6 Cef R | 0.39 | 0.78 | 2.5 |
| *Shigella flexneri* ATCC 11836 | 0.39 | 1.56 | 0.15 |
| *Citrobacter freundii* ATCC 8090 | 0.78 | 1.56 | — |
| *Pseudomonas aeruginosa* (6 strains) | 9.92 | — | — |
| Acinobacter | 0.78 | — | — |

Compound (1): (5R,6S)-6-[(1R)-hydroxyethyl]-2-(2-pyridinioethylthio) penem-3-carboxylate (Example 1)

Compound (31): (5R,6S)-6-[(1R)-hydroxyethyl]-2-[4-(pyridiniomethyl)phenoxyl]penem-3-carboxylate Example II).

Owing to their high antibacterial activity, the compounds of the invention are thus useful, for example, in the treatment of respiratory tract infections, for example, bronchitis, bronchopneumonia and pleuritis; hepatobiliary and abdominal infections; septicemia; urinary tract infections, for example, pyelonephritis and cystitis; obstetrical and gynecological infections, for instance, cervicitis and endometritis; and ear, nose and throat infections, for instance, otitis, sinusitis and parotitis.

The compounds of the invention may be administered, either to humans or to animals in a variety of dosage forms, e.g., orally in the form of tablets, capsules, drops or syrups; rectally in the form of suppositories; parenterally, e.g., intravenously or intramuscularly (as solutions or suspensions), with intravenous administration being preferred in emergency situation; by inhalation in the form of aerosols or solutions for nebulizers; intravaginally, e.g., in the form of bougies; or topically in the form of lotions, creams and ointments. The pharmaceutical or veterinary compositions containing the compounds of formula (I), which are also within the scope of the invention, may be prepared in a conventional way by employing the conventional carriers or diluents used for cephalosporins, for example.

Conventional carriers or diluents are, for example, water, gelatine, lactose, starches, magnesium stearate, talc, vegetable oils and cellulose. Daily doses in the range of about 0.5 to about 100 mg per kg of body weight may be used, in various animal species. The exact dose depends on the age, weight and condition of the subject to be treated and on the frequency and route of administration.

A preferred way of administration of the compounds of the invention is the parenteral one. In this case, the compounds may be administered, for example, to adult humans in an amount ranging from about 250 mg to about 1000 mg pro dose, preferably about 500 mg pro dose, 1–4 times a day, dissolved in a suitable solvent. Suitable solvents are, for example, sterile water or lidocaine hydrochloride solution for intramuscolar injections, and sterile water, physiological saline solution, dextrose solution or the conventional intravenous fluids or electrolytes, for intravenous injections.

Furthermore, the compounds of the invention may be used as antibacterial agents in a prophylactic manner in cleaning or as surface disinfecting compositions. The compounds of the invention are useful at a concentration of about 0.2 to 1% by weight of such compounds admixed with, suspended or dissolved in conventional inert dry or aqueous carriers for application by washing or spraying.

They are also useful as nutritional supplements in animal feeds.

Other features of the invention will become apparent in the course of the following descriptions of exemplary embodiments which are given for illustration of the invention and are not intended to be limiting thereof.

EXAMPLE 1

(5R,6S)-6-[(1R)-hydroxyethyl]-2-(2-pyridinioethylthio) penem-3-carboxylate (Compound 1)

A solution of 80% m-chloroperbenzoic acid (674 mg) in dichloromethane was added under stirring to a cooled ($-20°$ C.) solution of allyl (5R,6S)-6-[(1R)-tert-butyldimethylsilyloxyethyl]-2-(ethylthio)penem-3-carboxylate (0.88 g) in the same solvent (20 ml). After 20 minutes at $-20°$ C., a further amount of the oxidant (50 mg) was added, the solvent was removed in vacuo without external cooling and the residue was passed through a $SiO_2$ column, eluting with ethyl acetate-cyclohexane mixtures, to obtain allyl (5R,6S)-6-[(1R)-tert-butyldimethylsilyloxyethyl]-2-(ethylsulphynil)-penem-3-carboxylate as a syrup. This material (663 mg) was dissolved in acetonitrile and treated at $-40°$ C. under nitrogen with 2-mercaptoethanol (0.14 ml) and diisopropylethylamine (0.25 ml), in this sequence. After 15 minutes at $-40°$ C., the reaction mixture was quenched with acetic acid and partitioned between water and ethyl acetate. The organic extracts were concentrated and the residue purified by flash chromatography thereby obtaining allyl (5R,6S)-6-[(1R)-tert-butyldimethylsilyloxyethyl]-2-(2-hydroxyethylthio)-penem-3-carboxylate; IR: $\nu$ max $(CHCl_3)=s$ 3400, 1790, 1690 $cm^{-1}$; NMR(60 MHz, $CDCl_3 + D_2O$): δ 0.06 (6H, s, $SiMe_2$), 0.85 (9H, s, $SiBu^t$), 1.25 (3H, d, J=6.5 Hz, $CH_3CH$), 3.10 (2H, t, J=6 Hz, $SCH_2CH$), 3.65 (1H, dd, J=2 and 6 Hz, H-6), 3.80 (2H, t, J=6 Hz, $CH_2CH_2O$), 4.2 (1H, m, $CH_3\underline{CH}$), 4.75 (2H, br d, $CO_2\underline{CH_2}CH=$), 5.1 and 5.3 (2H, each m, $=CH_2$), 5.60 (1H, d, J=2 Hz, H-5), 5.7–6.2 (1H, m, $CH=CH_2$) ppm.

Trifluoromethanesulphonic anhydride (0.44 ml) and pyridine (0.47 ml) were added to a solution of the above intermediate (280 mg) in dry dichloromethane at $-40°$ C. in an argon atmosphere. The reaction mixture was warmed to $-15°$ C. and kept at this temperature until all the starting material had disappeared (TLC monitoring). A solution of 0.1M aqueous HCl (10 ml) was then added, the organic layer was separated, washed with a further amount of 0.1M HCL, dried and evaporated. The resulting residue, consisting of crude allyl (5R,6S)-6-[(1R)-tert-butyldimethylsilyloxyethyl]-2-pyridinioethylthio)penem-3-carboxylate chloride, was immediately dissolved in tetrahydrofuran (20 ml) and stirred for 24 hours at room temperature in the presence of acetic acid (1 ml) and tetrabutylammonium fluoride trihydrate (1.5 g). The solvent was removed in vacuo and the residue was purified by silica gel chromatography, eluting in sequence with $CH_2Cl_2$, $CH_2Cl_2$-MeCN, and aqueous MeCN, thereby obtaining the allyl ester of the title product; IR: $\nu$max (KBr)=3400, 1785, 1690 $cm^{-1}$. This material (120 mg) was stirred for 30 minutes at room temperature under nitrogen in a mixture of triphenylphosphine (20 mg) tetrakis (triphenylphosphine) palladium (20 mg), and acetic acid (0.15 ml) in 1:1 tetrahydrofurandichloromethane (8 ml). After filtering the catalyst, the solvent was removed and the residue dissolved in demineralized water, washed with dichloromethane, and passed through a reverse-phase column (LiChroprep® RP-18 Merck, water and then 10% aq MeCN as eluants). The product containing fractions were collected and freeze-dried to give the title compound (40 mg) as a white powder; UV: $\nu$max ($H_2O$)=320 nm; NMR (200 MHz, $D_2O$, 45° C.): δ1.26 (3H, d, J=6.5 Hz), 3.4–3.8 (2H, m) 3.80 (1H, dd, J=1.6 and 6.1 Hz), 4.20 (1H, dq, J=6.1 and 6.5 Hz), 4.8–5.1 (2H, m), 5.33 (1H, d, J=1.6 Hz), 8.08 (2H, dd, J=6.6 and 7.8 Hz), 8.64 (1H, t, J=7.8 Hz), 8.92 (2H, d, J=6.6 Hz); IR: (KBR) δmax=1590, 1630, 1765 $cm^{-1}$.

EXAMPLE 2

Operating as described in the previous example, the following compounds were analogously prepared:
(5R,6S)-6-[(1R)-hydroxyethyl]-2-[2-(3-methoxypyridinio) ethylthio]penem-3-carboxylate (2);
(5R,6S)-6-[(1R)-hydroxyethyl]-2-[2-(4-methylthiopyridinio)ethylthio]penem-3-carboxylate (3);
(5R,6S)-6-[(1R)-hydroxyethyl]-2-[2-(3-methylthiopyridinio)ethylthio]penem-3-carboxylate (4);
(5R,6S)-6-[(1R)-hydroxyethyl]-2-[2-(6,7-dihydro-5H-cyclopenta[b]pyridinio)ethylthio]penem-3-carboxylate (5);
(5R,6S)-6-[(1R)-hydroxyethyl]-2-[2-(N-methylpyrrolidinio)ethylthio]penem-3-carboxylate (6);
(5R,6S)-6-[(1R)-hydroxyethyl]-2-[2-(N,N,N-trimethylammonio)ethylthio]penem-3-carboxylate (7);
(5R,6S)-6-[(1R)-hydroxyethyl]-2-[2-(N-methylmorpholinio)ethylthio]penem-3-carboxylate (8);
(5R,6S)-6-[(1R)-hydroxyethyl]-2-(3-pyridiniopropylthio)penem-3-carboxylate (9);
(5R 6S)-6-[(1R)-hydroxyethyl]-2-[3-(N-methylpyrrolidinio)propylthio]penem-3-carboxylate (10); and
(5R,6S)-6-[(1R)-hydroxyethyl]-2-[1-(N-methylpyrrolidinio)cyclopentyl]penem-3-carboxylate (11).

EXAMPLE 3

(5R,6S)-6-[(1R)-hydroxyethyl]-2-[2-(3-methoxypyridinio)ethylthio]penem-3-carboxylate (Compound 2)

To a solution of allyl (5R,6S)-6-[(1R)-tert-butyldimethylsilyloxyethyl]-2-(2-hydroxyethylthio)penem-3-carboxylate (450 mg) in dry ethanol-free dichloromethane (15 ml) there were added, at −30° C. under nitrogen, triethylamine (0.175 ml) and methane sulphonylchloride (0.09 ml). The progress of the reaction was monitored by TLC. When the starting material had disappeared, the reaction mixture was washed with dilute aq. $NaHCO_3$ and then with water. The organic phase was separated, dried over $Na_2SO_4$ and evaporated to leave a residue which was purified by flash-chromatography (ethyl acetate-cyclohexane mixtures), thereby obtaining allyl (5R,6S)-6-[(1R)-tert-butyldimethylsilyloxyethyl]-2-(2-methanesulphonyloxyethylthio)penem-3-carboxylate. This compound (436 mg) was immediately dissolved in dry acetone (25 ml) and heated under argon in the presence of sodium iodide (260 mg) at 40° for several hours. When the reaction was over (NMR monitoring), the solvent was evaporated and the residue partitioned between water and ethyl acetate. Removal of the solvent from the dried organic layer left a residue consisting of crude allyl (5R,6S)-6-[(1R)-hydroxyethyl]-2-(2-iodoethylthio)penem-3-carboxylate, which was used as such in the following step.

A solution of the above intermediate in dry tetrahydrofuran (25 ml) was sequentially treated (ice-bath) with pyridine (0.2 ml) and silver perchlorat (175 mg). The reaction mixture was warmed to room temperature and the progress of the reaction was monitored, at 30 minute intervals, by TLC. Most of the solvent was then removed in vacuo and the residue was taken up in $CH_2Cl_2$ and washed with cold 0.05M aqueous perchloric acid and then with water.

The residue obtained from the dried organic layer was added to a solution of tetrabutylammonium fluoride trihydrate (1.7 g) in tetrahydrofuran (25 ml). Acetic acid (1 ml) was added and the mixture stirred overnight at room temperature. Removal of the solvent and flash chromatography over silica ($CH_2Cl_2$-MeCN, then aqueous MeCN) afforded a somewhat impure sample of the allyl ester of the title product, which was directly treated with triphenylphospine (30 mg), $(PPh_3)_2Pd$ (30 mg) and acetic acid (0.3 ml) in a tetrahydrofurandichloromethane mixture. The progress of the reaction was monitored by TLC; further amounts of $PPh_3$ and of the catalyst (5 mg each) were added at 5 minute intervals until the starting material had disappeared. The catalyst was filtered off and the residue obtained upon evaporation of the solvent was partitioned between water (1 ml) and dichloromethane (1 ml). The aqueous layer was collected and passed through a reverse-phase column, using water and finally aq. MeCN as eluants. Freeze-drying of the appropriate fractions gave the title compound (45 mg); IR: $\nu$max (KBR)=3400, 1755, 1605 $cm^{-1}$; NMR ($MH_z$, $D_2O$): δ1.31 (3H, d, J=6.5 Hz $CH_3CH$), 3.45 (2H, m, $CH_2S$), 3.97 (3H, s, OMe), 4.15 (1H, dd, J=1.3 and 6 Mz, H-6), 4.4 (1H, m, $CH_3H$/), 4.80 (2H, m, $CH_2N^+$), 5.70 (1H, d, J=1.3 Hz, H-5, H-5), 7.7–8.2 (2H, m,

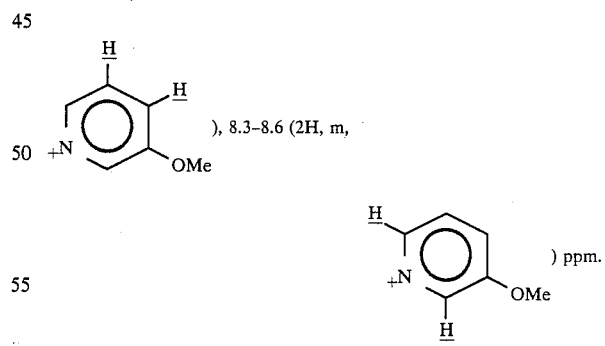

), 8.3–8.6 (2H, m, ) ppm.

EXAMPLE 4

Operating as described in the previous example, the following compounds were analogously prepared:
(5R,6S)-6-[(1R)-hydroxyethyl]-2-(2-pyridinioethylthio)penem-3-carboxylate (1);
(5R,6S)-6-[(1R)-hydroxyethyl]-2-[2-(N-methylpyrrolidinio)ethylthio]penem-3-carboxylate (6);
(5R,6S)-6-[(1R)-hydroxyethyl]-2-(2-pyridiniopropylthio)penem-3-carboxylate (9); and (5R,6S)-6-[(1R)-hydroxyethyl]-2-[3-(N-methylpyrrolidinio)propylthio]penem-3-carboxylate (10).

EXAMPLE 5

(5R,6S)-6-[(1R)-hydroxyethyl]-2-[2-(N-methylmorpholinio)ethylthio]penem-3-carboxylate (Compound 8)

A solution of allyl (5R,6S)-6-[(1R)-tert-butyldimethylsilyloxyethyl]-2-(ethylsulphynyl)penem-3carboxylate (prepared as described in Example 1) (230 mg) in dry acetonitrile (5 ml) was cooled under argon to −60° C. and treated in sequence with N-(2-mercaptoethyl)-N-methylmorpholinio trifluoromethanesulphonate (176 mg) and diisopropylethylamine (0.12 ml). The reaction mixture was stirred for 30 minutes at −40° C. and then partitioned between 0.1N HCl and dichloromethane. The organic layer was washed with brine and the solvent removed, thus obtaining crude allyl (5R,6S)-6-[(1R)-tert-butyldimethylsilyloxyethyl]-2-[2-(N-methylmorpholinio)ethylthio]penem-3-carboxylate (chloride, trifluoromethanesulphonate salts) as a gum. This material was stirred with tetrabutylammonium fluoride trihydrate (470 mg) and acetic acid (0.5 ml) in tetrahydrofuran (10 ml) for 18 hours at room temperature. After evaporation of the solvent, the residue was loaded on a silica column.

Elution with $CH_2Cl_2$, then $CH_2Cl_2$-EtOH, then EtOH-MeCN, and finally 35% aq. MeCN followed by removal of the solvent from the appropriate fractions, gave an aqueous solution of the allyl ester of the title product.

After washing with ether and freeze-drying, the obtained powder was taken up in tetrahydrofuran dichloromethane (1:1, 10 ml), $PPh_3$ (50 mg), $(PPh_3)_4Pd$ (50 mg), and acetic acid (0.2 ml) were added, and the mixture stirred for 1 hour at room temperature. The catalyst was filtered off and the solvent evaporated. The residue was dissolved in demineralized water (1 ml), washed with ethyl acetate (1 ml), and the aqueous solution passed through a reverse phase column (LiChroprep® RP-18 Merck). Elution with water and then with acetonitrile-water, followed by freeze-drying of the appropriate fractions, gave the title product as a white powder (40 mg); IR: $\nu$max (KBr)=3400, 1760, 1605, 1570 cm$^{-1}$; NMR (60 MHz, $D_2O$): δ1.29 (3H, d, J=6.5 Hz, $\underline{CH_3}$CH), 3.2 (3H, s, $CH_3N^+$), 3.1–4.1 (13H, m, $CH_2S$, morpholinio, $CH_2^+N$ and H-6), 4.25 (1H, m, $CH_3\underline{CH}$), 5.75 (1H, d, J=1.5 Hz, H-5) ppm.

EXAMPLE 6

Operating as described in the previous example, the following compounds were analogously prepared:
(5R, 6S)-6-[(1R)-hydroxyethyl]-2-(2-pyridinioethylthio)penem-3-carboxylate (1);
(5R,6S)-6-[(1R)-hydroxyethyl]-2-[2-(3-methylthiopyridinio)ethylthio]penem-3-carboxylate (4);
(5R,6S)-6-[(1R)-hydroxyethyl]-2-[2-(N-methylpyrrolidinio)ethylthio]penem-3-carboxylate (6); and
(5R,6S)-6-[(1R)-hydroxyethyl]-2-(3-pyridiniopropylthio)penem-3-carboxylate (9).

EXAMPLE 7

(5R,6S)-6-[(1R)-hydroxyethyl]-2-[4-(pyridiniomethyl)phenylthio]penem-3-carboxylate (Compound 12)

A solution of allyl (5R,6S)-6-[(1R)-tert-butyldimethylsilyloxyethyl]-2-[4-(hydroxymethyl)phenylthio]-penem-3-carboxylate (450 mg) in dry dichloromethane (20 ml) was stirred under argon with pyridine (0.7 ml) and trifluoromethanesulphonic anhydride (0.66 ml) at −40° C. for 30 minutes. The reaction mixture was poured into 0.1M HCl and the organic layer separated, washed with brine and evaporated. To the resulting gum there were added tetrahydrofuran (15 ml), acetic acid (1.5 ml), and tetrabutylammonium fluoride trihydrate (1.5 g). When the starting material had disappeared (TLC monitoring, about 1 day at room temperature), the solvent was evaporated in vacuo and the residue was purified by flash chromatography over $SiO_2$ ($CH_2Cl_2$-MeCN and then aqueous MeCN as eluants) to afford salts (chloride, acetate) of allyl (5R,6S)-6-[(1R)-hydroxyethyl]-2-[4-(pyridiniomethyl)phenylthio]penem-3-carboxylate (220 mg); IR: $\nu$ max (film)=3400, 1785, 1705 cm$^{-1}$. This material was taken up in a mixture of $PPh_3$ (23 mg), $(PPh_3)_4$ Pd (23 mg) and acetic acid (0.3 ml) in tetrahydrofuran-dichloroetane (1:1, 15 ml). More catalyst was added at ten minutes intervals, until the reaction was judged complete by TLC. The mixture was filtered, the solvent removed in vacuo and the residue purified by reverse-phase chromatography, eluting first with water and then with a gradient in acetonitrile. The β-lactam-containing fractions (UV>300 nm) were collected and freeze-dried to give the title compound as a white amorphous solid (95 mg); IR: $\nu$ max (KBr)=3400, 1760, 1600 cm$^{-1}$.

EXAMPLE 8

Operating as described in the previous example, the following compounds were analogously obtained:
(5R,6S)-6-[(1R)-hydroxyethyl]-2-[4-(4-methylthiopyridiniomethyl)phenylthio]penem-3-carboxylate (13);
(5R,6S -6-[(1R)-hydroxyethyl]-2-[4-(3-methoxypyridiniomethyl)phenylthio]penem-3-carboxylate (14);
(5R,6S)-6-[(1R)-hydroxyethyl]-2-[4-(3-methylthiopyridiniomethyl)phenylthio]penem-3-carboxylate (15);
(5R,6S)-6 [(1R)-hydroxyethyl]-2-[4-(2-methyl-5-ethylpyridiniomethyl)phenylthio]penem-3-carboxylate (16);
(5R,6S)-6-[(1R)-hydroxyethyl]-2-[4-(3-cyanomethylpyridiniomethyl)phenylthio]penem-3-carboxylate (19);
(5R,6S)-6-[(1R)-hydroxyethyl]-2-[4-(6,7-dihydro-5H-cyclopenta[b]pyridiniomethyl)phenylthio]penem-3-carboxylate (20);
(5R,6S)-6-[(1R)-hydroxyethyl]-2-[4-(N-methylpyrrolidiniomethyl)phenylthio]penem-3-carboxylate (21);
(5R,6S)-6-[(1R)-hydroxyethyl]-2-[4-(N-methylpiperidiniomethyl)phenylthio]penem-3-carboxylate (22);
(5R,6S)-6-[(1R)-hydroxyethyl]-2-[4-(N-methylmorpholiniomethyl)phenylthio]penem-3-carboxylate (23);
(5R,6S)-6-[(1R)-hydroxyethyl]-2-[4-(N,N,N-triethylammoniomethyl)phenylthio]penem-3-carboxylate (24);
(5R,6S)-6-[(1R)-hydroxyethyl]-2-[4-(N,N,N-trimethylammoniomethyl)phenylthio]penem-3-carboxylate (25);
(5R,6S)-6-[(1R)-hydroxyethyl]-2-[2-(pyridiniomethyl)phenylthio]penem-3-carboxylate (26);
(5R,6S)-6-[(1R)-hydroxyethyl]-2-[2-(N-methylpyrrolidiniomethyl)phenylthio]penem-3-carboxylate (27);

(5R,6S)-6-[(1R)-hydroxyethyl]-2-[3-(pyridiniomethyl)-phenylthio]penem-3-carboxylate (28);
(5R,6S)-6-[(1R)-hydroxyethyl]-2-[3-(N-methyl-piperidiniomethyl)phenylthio]penem-3-carboxylate (29); and
(5R,6S)-6-[(1R)-hydroxyethyl]-2-[3-(N,N,N-trimethylammoniomethyl)phenylthio]penem-3-carboxylate (30).

EXAMPLE 9

(5R,6S)-6-[(1R)-hydroxyethyl]-2-[4-(4-carbamoyl-pyridiniomethyl)phenylthio]penem-3-carboxylate (Compound 17)

Allyl (5R,6S)-6-[(1R)-tert-butyldimethylsilyloxyethyl]-2-(4-hydroxymethylphenylthio)penem-3-carboxylate was converted into allyl (5R,6S)-6-[(1R)-tert-butyldimethylsilyloxyethyl]-2-(4-iodomethylphenylthio)-penem-3-carboxylate by closely following the procedure described in Example 2. Without purification, this intermediate (250 mg) was dissolved in dry dimethylformamide and stirred at $-20°$ C. under nitrogen with nicotinamide (500 mg) and silver perchlorate (120 mg). The reaction mixture was warmed to room temperature while monitoring the progress of the reaction by TLC. Partition between dichloromethane and 0.05M aqueous hydrochloric acid followed by washing of the organic layer with water and then brine, gave a solution of allyl (5R,6S)-6-[(1R)-tert-butyldimethylsilyloxyethyl]-2-[4-(4-carbamoylpyridiniomethyl)phenylthio]penem-3-carboxylate; IR: $\nu$ max (film)=1795, 1705 sh, 1685 cm$^{-1}$.

Desilylation of this material with tetrabutylammonium fluoride followed by deallylation with (PPh$_3$)$_4$Pd, as indicated in Example 7, furnished the title compound; IR: $\nu$ max (KBr)=3400, 1765, 1610 cm$^{-1}$.

EXAMPLE 10

Operating as described in the previous example, the following compound was analogously obtained:
(5R,6S)-6-[(1R)-hydroxyethyl]-2-[4-(3-hydroxymethyl-pyridinio methyl)phenylthio]penem-3-carboxylate (18).

EXAMPLE 11

(5R,6S)-6-[(1R)-hydroxyethyl]-2-[4-pyridiniomethyl) phenoxy]penem-3-carboxylate (Compound 31)

A solution of p-nitrobenzyl (5R,6S)-6-[(1R)-tert-butyldimethylsilyloxyethyl]-2-[4-(hydroxymethyl)-phenoxy]penem-3-carboxylate (320 mg) in dry dichloromethane (15 ml) was cooled at $-70°$ C. under nitrogen. Pyridine (1.5 ml) and trifluoromethanesulphonic anhydride (0.8 ml) were added in sequence, and the mixture was warmed to $-30°$ C. The reaction mixture was sequenced with 0.1N aqueous HCl and the separated organic layer was washed once with water then dried (Na$_2$SO$_4$), concentrated to a small volume and taken up in dry tetrahydrofuran (20 ml). To this solution, acetic acid (1 ml) and tetrabutylammonium fluoride trihydrate (1.0 g) were added, and the mixture stirred for 20 hours at room temperature. Removal of the solvent and flash-chromatography over silica (aq. MeCN) afforded the p-nitrobenzyl ester of the title product; IR: $\nu$ max (film)=3400, 1790, 1710 cm$^{-1}$.

This intermediate (200 mg) was taken up in a mixture of tetrahydrofuran (20 ml) and aq. NH$_4$Cl (5 g in 20 ml). Iron powder (5 g) was added and the mixture vigorously stirred at 10°-15° C. until the reaction was judged complete by TLC (H$_2$O-MeOH-NaCl 9:1:1). The mixture was filtered, and the solvent was evaporated in vacuo to leave an aqueous solution of the crude title compound, which was isolated pure after reverse-phase chromatography (LiChroprep® RP-18 Merck) as a white powder (80 mg); IR: $\nu$ max (KBr=3400, 1760, 1600 cm$^{-1}$.

UV: $\lambda$ max (H$_2$O)=260, 303 nm

NMR (200 MHz D$_2$O, 45° C.): δ 1.33 (3H, d, J=6.5 Hz), 3.89 (1H, dd, J=1.6 and 6.1 Hz), 4.27 (1H, dq, J=6.1 and 6.5 Hz), 5.69 (1H, d, J=1.6 Hz), 5.85 (2H, s), 7.54, 7.32 (each 2H, m), 8.13 (2H, dd, j=6.6 and 7.8 Hz), 8.62 (1H, t, J=7.8 Hz), 8.94 (2H, d, J=6.6 Hz).

EXAMPLE 12

Operating as described in the previous example, the following compounds were analogously obtained:
(5R,6S)-6-[(1R)-hydroxyethyl]-2-[4-(3-cyanomethyl-pyridiniomethyl)phenoxy]penem-3-carboxylate (32);
(5R,6S)-6-[(1R)-hydroxyethyl]-2-[4-(3-methylthi-opyridiniomethyl)phenoxy]penem-3-carboxylate (33);
(5R,6S)-6-[(1R)-hydroxyethyl]-2-[4-(3-methoxypyridiniomethyl)phenoxy]penem-3-carboxylate (34);
(5R,6S)-6-[(1R)-hydroxyethyl]-2-[4-(N,N,N-triethylammoniomethyl)phenoxy]penem-3-carboxylate (35);
(5R,6S)-6-[(1R)-hydroxyethyl]-2-[4-(N-methylpyrrolidiniomethyl)phenoxy]penem-3-carboxylate (36);
(5R,6S)-6-[(1R)-hydroxyethyl]-2-[4-(N-methylmorpholiniomethyl)phenoxy]penem-3-carboxylate (37);
(5R,6S)-6-[(1R)-hydroxyethyl]-2-[2-(pyridiniomethyl)-phenoxy]penem-3-carboxylate (38);
(5R,6S)-6-[(1R)-hydroxyethyl]-2-[3-(pyridiniomethyl)-phenoxy]penem-3-carboxylate (39);
(5R,6S)-6-[(1R)-hydroxyethyl]-2-[4-(4-methoxypyridiniomethyl)phenoxy]penem-3-carboxylate (40); and
(5R,6S)-6-[(1R)-hydroxyethyl]-2-[4-(2-methoxypyridinio)phenoxy]penem-3-carboxylate (41).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of formula I:

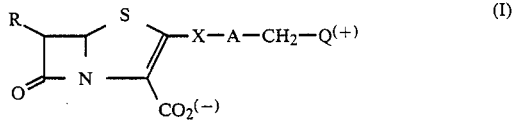

wherein:

X is a sulphur atom or an oxygen atom;

R is a hydrogen atom or a C$_1$-C$_4$ alkyl group which is unsubstituted or substituted by at least one substitute selected from the group consisting of a free hydroxy group, protected hydroxy groups and halogen atoms;

A is a Z, Z—Z—CO— or —Z—CO— residue, wherein Z is (a) a substituted or unsubstituted phenylene or naphthylene group, (b)

(c) an aralkylene radical of the formula

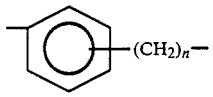

wherein
n is 1, 2 or 3; and
$Q^{(+)}$ is a $^+NR_1R_2R_3$ group, wherein
(i) $R_1$, $R_2$ and $R_3$ are each independently a substituted or unsubstituted $C_{1-4}$alkyl, $C_{7-11}$ aralkyl, phenyl or naphthyl; or (ii) $R_1$ is as defined above under (i) and $R_2$ and $R_3$ taken together with the nitrogen atom to which they are both bound represent a substituted or unsubstituted heterocyclic ammonium radical of the formula

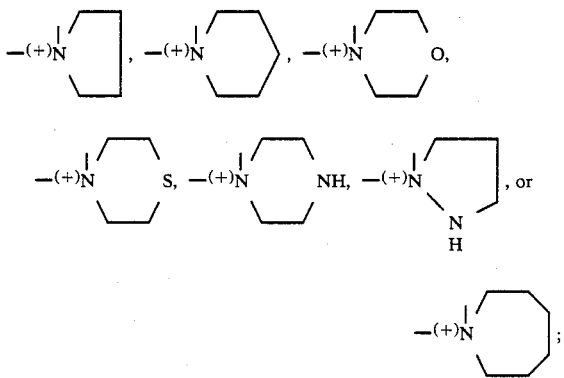

or (iii) $R_1$, $R_2$, and $R_3$ taken together with the nitrogen atom to which they are all bound, represent a substituted or unsubstituted azoniabicyclo or azoniatricyclo radical; or (iv) $R_1$, $R_2$ and $R_3$, taken together with the nitrogen atom to which they are all bound, represent a substituted pyridinium, pyrazinium, pyrazolium, or pyridazinium radical; or an unsubstituted pyridinium, pyrazinium pyrazolium, pyridinium, pyrazinium, pyrazolium, and
wherein the substituents for said alkyl, aralkyl, phenyl, naphthyl, azoniabicyclo, azoniatricyclo, pyridinium, pyrazinium, pyrazolium, pyridazinium, cycloalkylene, alkylene, phenylene, naphthylene and heterocyclediyl radicals are selected from the group consisting of: (a) halogen atoms; (b) hydroxy; (c) $C_1$-$C_4$ alkoxies; (d) $C_1$-$C_4$ alkylthios; (e) groups —$NR_4R_5$ where each of $R_4$ and $R_5$ is, independently, hydrogen or a $C_1$-$C_4$ alkyl; (f) sulfos; (g) —$CO_2R_4$ where $R_4$ is as defined above; (h) —C≡N; (i) dimethyl-formimidino; (j) groups —CO—$NR_4R_5$ where $R_4$ and $R_5$ are as defined above; (k) carbamoyloxies;
(1) a hydroxyiminomethyl (HO—N=CH—) or methoxyiminomethyl (CH$_3$O—N=CH—) groups; (m) formamido and acetoamido groups; (n) formyloxy and acetoxy groups; (o) $C_1$-$C_4$ alkanoyl groups; (p) phenyl or naphthyl groups; (q) nitro groups; (r) mesyloxy groups; (s) oxo groups; and (t) $C_1$-$C_4$ alkyl groups and $C_1$-$C_4$ alkyl groups substituted by a substitute chosen from (a) to (s) above.

2. The compound of claim 1 wherein R is an (α-hydroxy)ethyl group.

3. The compound of claim 1, wherein Z is a group of the formula

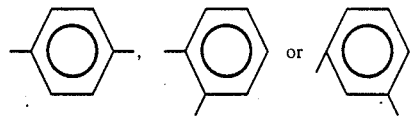

4. The compound of claim 1, wherein $R_1$, $R_2$ and $R_3$ are each independently selected from the group consisting of: methyl, ethyl, n-propyl, i-propyl, dimethylaminomethyl, cyanomethyl, cyanoethyl, carbamoylmethyl, 2-hydroxyethyl, 2-chloroethyl, carboxymethyl, ethoxycarbonylmethyl, carboxyethyl, 2-methyl-2-cyanoethyl, 3-oxobutyl and dimethylformimidino groups (—C(NMe$_2$)=NH).

5. The compound of claim 1, wherein X is a sulphur atom.

6. The compound of claim 5, said compound being (5R,6S)-6-[(1R)-hydroxyethyl]-2-[4-(N,N,N-triethylammoniomethyl)phenylthio]penem-3-carboxylate, (5R,6S)-6-[(1R)-hydroxyethyl]-2-[4-(N,N,N-trimethylammoniomethyl)phenylthio]penem-3-carboxylate;
or (5R,6S)-6-[(1R)-hydroxyethy]-2-[3-(N,N,N-triethylammoniomethyl)phenylthio]penem-3-carboxylate.

7. The compound of claim 1 wherein X is an oxygen atom.

8. The compound of claim 7, said compound being (5R,6S)-6-[(1R)-hydroxyethyl]-2-[4-(N,N,N-triethylammoniomethyl)phenoxy]penem-3-carboxylate.

9. The compound of claim 1, wherein $R_1$, $R_2$ and $R_3$ taken together with the nitrogen atom to which all are bound, is a radical selected from the group consisting of

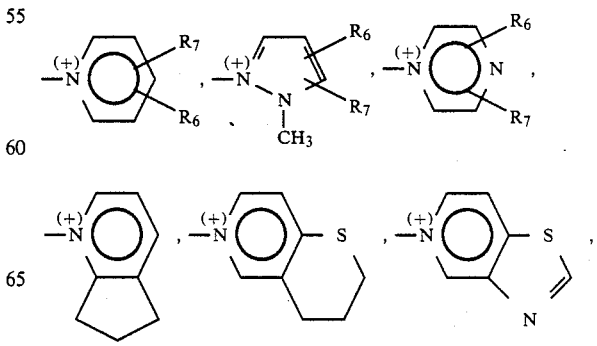

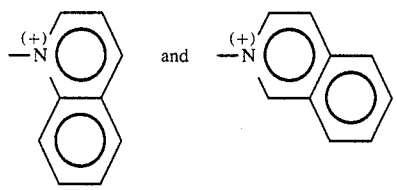 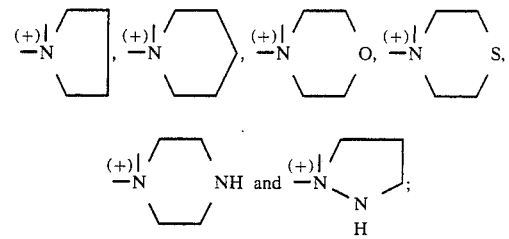

wherein R₆ and R₇ are each independently a hydrogen atom, $C_1$–$C_4$ alkyl, methoxy, methylthio, cyanomethyl, hydroxymethyl, methylsulphonyl or carbamoyl group.

10. The compound of claim 9, wherein X is a sulphur atom.

11. The compound of claim 10, said compound being (5R,6S)-6-[(1R)-hydroxyethyl]-2-[4-pyridiniomethyl)-phenylthio]penem-3-carboxylate,
(5R,6S)-6-[(1R)-hydroxyethyl]-2-[4-(4-methylthiopyridiniomethyl)phenylthio]penem-3carboxylate,
(5R,6S)-6-[(1R)-hydroxyethyl]-2-[4-(3-methoxypyridiniomethyl)phenylthio]penem-3-carboxylate,
(5R,6S)-6-[(1R)-hydroxyethyl]-2-[4-(3-methylthiopyridiniomethyl)phenylthio]penem-3-carboxylate,
(5R,6S)-6-[(1R)-hydroxyethyl]-2-[4-(2-methyl-5-ethyl-pyridiniomethyl)phenylthio]penem-3-carboxylate,
(5R,6S)-6-[(1R)-hydroxyethyl]-2-[4-(4-carbamoyl-pyridiniomethyl)phenylthio]penem-3-carboxylate,
(5R,6S)-6-[(1R)-hydroxyethyl]-2-[4-(3-hydroxymethyl-pyridiniomethyl)phenylthio]penem-3-carboxylate,
(5R,6S)-6-[(1R)-hydroxyethyl]-2-[4-(3-cyanomethyl-pyridiniomethyl)phenylthio]penem-3-carboxylate,
(5R,6S)-6-[(1R)-hydroxyethyl]-2-[4-(6,7-dihydro-5H-cyclopenta[b]pyridiniomethyl)phenylthio]penem-3-carboxylate,
(5R,6S)-6-[(1R)-hydroxyethyl]-2-[2-(pyridiniomethyl)-phenylthio]penem-3-carboxylate, or
(5R,6S)-6-[(1R)-hydroxyethyl]-2-[3-(pyridiniomethyl)-phenylthio]penem-3-carboxylate.

12. The compound of claim 9, wherein X is an oxygen atom.

13. The compound of claim 12, said compound being (5R,6S)-6-[(1R)-hydroxyethyl]-2-[4-(pyridiniomethyl)-phenoxy]penem-3-carboxylate,
(5R,6S)-6-[(1R)-hydroxyethyl]-2-[4-(3-cyanomethyl-pyridiniomethyl)phenoxy]penem-3-carboxylate;
(5R,6S)-6-[(1R)-hydroxyethyl]-2-(4-(3-methylthiopyridiniomethyl)phenoxy]penem-3-carboxylate,
(5R,6S)-6-[(1R)-hydroxyethyl]-2-[4-(3-methoxypyridiniomethyl)phenoxy]penem-3-carboxylate,
(5R,6S)-6-[(1R)-hydroxyethyl]-2-[2-(pyridiniomethyl)-phenoxy]penem-3-carboxylate, or
(5R,6S)-6-[(1R)-hydroxyethyl]-2-[3-(pyridiniomethyl)-phenoxy]penem-3-carboxylate.

14. The compound of claim 1, wherein $R_1$ is selected from the group consisting of methyl, ethyl, n-propyl, i-propyl, dimethylaminomethyl, cyanomethyl, cyanoethyl, carbamoylmethyl, 2-hydroxyethyl, 2-chloroethyl, carboxymethyl, ethoxycarbonylmethyl, carboxyethyl, 2-methyl-2-cyanoethyl, 3-oxobutyl and dimethylformimidino groups, and R₂ and R₃ taken together with the nitrogen atom to which both are bound, represent a heterocyclyl ammonium radical selected from the group consisting of and wherein said heterocycle ammonium radical is unsubstituted or substituted by at least one substituent selected from the group consisting of a halogen atom, hydroxy, amino, cyano, dimethylformimidino, ethoxycarbonyl, oxo, $C_1$–$C_4$ alkyl and alkanoyl groups.

15. The compound of claim 14, wherein $R_1$ is a methyl, ethyl, chloroethyl, cyanomethyl, cyanoethyl, aminoethyl, or hydroxyethyl group.

16. The compound of claim 14, wherein X is a sulphur atom.

17. The compound of claim 16, said compound being (5R,6S)-6-[(1R)-hydroxyethyl]-2-[4-(N-methylpyrrolidiniomethyl)phenylthio]penem-3-carboxylate,
(5R,6S)-6-[(1R)-hydroxyethyl]-2-[4-(N-methyl-piperidiniomethyl)phenylthio]penem-3-carboxylate,
(5R,6S)-6-[(1R)-hydroxyethyl]-2-[4-(N-methylmorpholiniomethyl)phenylthio]penem-3-carboxylate,
(5R,6S)-6-[(1R)-hydroxyethyl]-2-[2-(N-methylpyrrolidiniomethyl)phenylthio]penem-3-carboxylate, or
(5R,6S)-6-[(1R)-hydroxyethyl]-2-[3-(N-methyl-piperidiniomethyl)phenylthio]penem-3-carboxylate.

18. The compound according to claim 14 wherein X is an oxygen atom.

19. The compound of claim 18, said compound being (5R,6S)-6-[(1R)-hydroxyethyl]-2-[4-(N-methylpyrrolidiniomethyl)phenoxy]penem-3-carboxylate, or
(5R,6S)-6-[(1R)-hydroxyethyl]-2-[4-(methylmorpholiniomethyl)phenoxy)penem-3-carboxylate.

20. A pharmaceutical antibiotic composition, comprising an antibiotically effective amount of a compound of claim 1 or a pharmaceutically acceptable salt thereof, and a pharmaceutically acceptable excipient.

21. A veterinary antibiotic composition, comprising an antibiotically effective amount of a compound of claim 1 or a veterinarily acceptable salt thereof, and a veterinarily acceptable excipient.

22. A method of treating a bacterial infection, comprising administering to a patient in need thereof an antibacterial effective amount of a compound of claim 1 or a pharmaceutically or veterinarily acceptable salt thereof.

23. A method of treating bronchitis, comprising administering to a patient in need thereof, and anti-bronchitis effective amount of a compound of claim 1 or a pharmaceutically or veterinarily acceptable salt thereof.

24. A method of treating bronchopneumonia comprising administering to a patient in need thereof an anti-bronchopneumonia effective amount of a compound of claim 1 of a pharmaceutically or veterinarily acceptable salt thereof.

25. A method of treating pleuritis, comprising administering to a patient in need thereof an anti-pleuritis effective amount of a compound of claim 1 or a pharmaceutically or veterinarily acceptable salt thereof.

26. A method of treating hepatobiliary infection, comprising administering to a patient in need thereof an amount of a compound of claim 1 or a pharmaceutically or veterinarily acceptable salt thereof effective for the treatment of hepatobiliary infection.

27. A method of treating abdominal infection, comprising administering to a patient in need thereof an amount of a compound of claim 1 or a pharmaceutically or veterinarily acceptable salt thereof effective for the treatment of abdominal infection.

28. A method of treating septicemia, comprising administering to a patient in need thereof an anti-septicemia effective amount of a compound of claim 1 or a pharmaceutically or veterinarily acceptable salt thereof.

29. A method of treating pyelonephritis, comprising administering to a patient in need thereof an anti-pyelonephritis effective amount of a compound of claim 1 or a pharmaceutically or veterinarily acceptable salt thereof.

30. A method of treating cystitis, comprising administering to a patient in need thereof an anti-cystitis effective amount of a compound of claim 1 or a pharmaceutically or veterinarily acceptable salt thereof.

31. A method of treating cervicitis, comprising administering to a patient in need thereof an anti-cervicitis effective amount of a compound of claim 1 or a pharmaceutically or veterinarily acceptable salt thereof.

32. A method of treating endometritis, comprising administering to a patient in need thereof an anti-endometritis effective amount of a compound of claim 1 or a pharmaceutically or veterinarily acceptable salt thereof.

33. A method of treating otitis, comprising administering to a patient in need thereof an anti-otitis effective amount of a compound of claim 1 or a pharmaceutically or veterinarily acceptable salt thereof.

34. A method of treating sinusitis, comprising administering to a patient in need thereof an anti-sinusitis effective amount of a compound of claim 1 or a pharmaceutically or veterinarily acceptable salt thereof.

35. A method of treating parotitis, comprising administering to a patient in need thereof an anti-parotitis effective amount of a compound of claim 1 or a pharmaceutically or veterinarily acceptable salt thereof.

* * * * *